(12) United States Patent
Benedict et al.

(10) Patent No.: US 10,524,774 B2
(45) Date of Patent: Jan. 7, 2020

(54) METHOD OF REPAIRING CARTILAGE DEFECTS (71) Applicant: ARTHREX, INC., Naples, FL (US)

(72) Inventors: Robert Benedict, Fort Myers, FL (US); Brandon Roller, Naples, FL (US); Reinhold Schmieding, Naples, FL (US); Marc Stoll, Fort Myers, FL (US)

(73) Assignee: ARTHREX, INC., Naples, FL (US)

( * ) Notice: Subject to any disclaimer, the term of this patent is extended or adjusted under 35 U.S.C. 154(b) by 412 days.

(21) Appl. No.: 14/677,080

(22) Filed: Apr. 2, 2015

(65) Prior Publication Data
US 2016/0287243 A1 Oct. 6, 2016

(51) Int. Cl.
A61B 17/04 (2006.01)

(52) U.S. Cl.
CPC .. *A61B 17/0401* (2013.01); *A61B 2017/0412* (2013.01); *A61B 2017/0414* (2013.01);
(Continued)

(58) Field of Classification Search
CPC . A61B 17/0401; A61B 17/04; A61B 17/0466; A61B 17/84; A61B 17/842; A61B 17/844; A61B 2017/0403; A61B 2017/0404; A61B 2017/0406; A61B 2017/0408; A61B 2017/0409; A61B 2017/0411; A61B 2017/0412; A61B 2017/0414; A61B 2017/0416; A61B 2017/0417; A61B 2017/0419; A61B 2017/042; A61B 201/0422; A61B 2017/0424; A61B 2017/0425; A61B 2017/0427; A61B 2017/044; A61B 2017/0441; A61B 2017/0443; A61B 2017/0445; A61B 2017/0446; A61B 2017/0448; A61B 2017/048; A61B 2017/0451; A61B 2017/0453; A61B 2017/0454; A61B 2017/0456; A61B 2017/0458; A61B 2017/0459; A61B 2017/0461; A61B 2017/0429; A61B 2017/043; A61B 2017/0432; A61B 2017/0433; A61B 2017/0435; A61B 2017/0437; A61B 2017/0438; A61B 2017/0462; A61B 2017/06185; A61B 2017/0464; A61F 2/0811; A61F 2002/0817; A61F 2002/0823; A61F 2002/0829; A61F 2002/0835; A61F 2002/0841;
(Continued)

(56) References Cited

U.S. PATENT DOCUMENTS 3,318,774 A 5/1967 Dingwall
4,772,286 A 9/1988 Goble et al.
(Continued)

OTHER PUBLICATIONS

International Search Report and Written Opinion for PCT Application No. PCT/US2015/059192, dated Feb. 3, 2016.
(Continued)

*Primary Examiner* — Katherine H Schwiker
(74) *Attorney, Agent, or Firm* — Carlson, Gaskey & Olds (57) ABSTRACT A method for repairing a cartilage defect according to an exemplary aspect of the present disclosure includes, among other things, preparing a cartilage defect for implantation of a cartilage graft and attaching the cartilage graft to bone using at least one knotless suture anchor.

2 Claims, 6 Drawing Sheets (52) U.S. Cl.
CPC .............. *A61B 2017/0445* (2013.01); *A61B 2017/0451* (2013.01); *A61B 2017/0458* (2013.01)

(58) Field of Classification Search
CPC ...... A61F 2002/0847; A61F 2002/0852; A61F 2002/0858; A61F 2002/0864; A61F 2002/087; A61F 2002/0876; A61F 2002/0885; A61F 2002/0888
See application file for complete search history.

(56) References Cited

U.S. PATENT DOCUMENTS

| | | | |
|---|---|---|---|
| 4,773,910 A | 9/1988 | Chen et al. | |
| 5,139,520 A | 8/1992 | Rosenberg | |
| 5,713,374 A | 2/1998 | Pachence et al. | |
| 5,964,764 A | 10/1999 | West, Jr. et al. | |
| 6,440,141 B1 * | 8/2002 | Philippon | A61B 17/1615 604/60 |
| 6,488,033 B1 | 12/2002 | Cerundolo | |
| 7,326,222 B2 | 2/2008 | Dreyfuss et al. | |
| 7,361,195 B2 | 4/2008 | Schwartz et al. | |
| 7,371,260 B2 | 5/2008 | Malinin | |
| 7,488,347 B1 | 2/2009 | Goble et al. | |
| 7,641,694 B1 * | 1/2010 | Goble | A61F 2/30749 623/18.11 |
| 7,666,230 B2 | 2/2010 | Orban et al. | |
| 7,749,250 B2 | 7/2010 | Stone et al. | |
| 7,901,461 B2 | 3/2011 | Harmon et al. | |
| 7,931,695 B2 | 4/2011 | Ringeisen | |
| 8,012,205 B2 | 9/2011 | Plouhar et al. | |
| 8,016,867 B2 | 9/2011 | Bowman | |
| 8,062,654 B2 | 11/2011 | Nelson et al. | |
| 8,142,502 B2 | 3/2012 | Stone et al. | |
| 8,444,968 B2 | 5/2013 | Seyedin et al. | |
| 8,449,561 B2 | 5/2013 | Bowman | |
| 8,518,433 B2 | 8/2013 | Kizer et al. | |
| 8,524,268 B2 | 9/2013 | Kizer et al. | |
| 8,535,703 B2 | 9/2013 | Schmieding et al. | |
| 8,545,535 B2 | 10/2013 | Hirotsuka et al. | |
| 8,597,352 B2 | 12/2013 | Schwartz | |
| 8,637,066 B2 | 1/2014 | Binnette et al. | |
| 8,641,775 B2 | 2/2014 | Harmon et al. | |
| 8,657,881 B2 | 2/2014 | Kladakis et al. | |
| 8,734,828 B2 | 5/2014 | Kaps et al. | |
| 8,834,568 B2 | 9/2014 | Shapior | |
| 8,834,914 B2 | 9/2014 | Kizer et al. | |
| 8,882,774 B2 | 11/2014 | Malinin | |
| 8,895,045 B2 | 11/2014 | Jamiolkowski et al. | |
| 9,066,716 B2 | 6/2015 | Sikora et al. | |
| 9,855,146 B2 | 1/2018 | Schmieding | |
| 2004/0093031 A1 | 5/2004 | Burkhart et al. | |
| 2005/0149118 A1 * | 7/2005 | Koyfman | A61B 17/0401 606/228 |
| 2006/0293710 A1 * | 12/2006 | Foerster | A61B 17/0401 606/232 |
| 2007/0135843 A1 * | 6/2007 | Burkhart | A61B 17/0401 606/232 |
| 2007/0288023 A1 * | 12/2007 | Pellegrino | A61B 17/0401 606/232 |
| 2008/0039954 A1 | 2/2008 | Long et al. | |
| 2008/0125863 A1 | 5/2008 | McKay | |
| 2008/0195205 A1 | 8/2008 | Schwartz | |
| 2008/0255613 A1 * | 10/2008 | Kaiser | A61B 17/0401 606/232 |
| 2008/0269674 A1 | 10/2008 | Stone | |
| 2008/0281422 A1 | 11/2008 | Schmieding | |
| 2009/0024229 A1 | 1/2009 | Chen et al. | |
| 2009/0312842 A1 | 12/2009 | Bursac et al. | |
| 2010/0016892 A1 * | 1/2010 | Kaiser | A61B 17/0401 606/232 |
| 2010/0040662 A1 | 2/2010 | Cotton et al. | |
| 2010/0168869 A1 * | 7/2010 | Long | A61F 2/08 623/23.72 |
| 2011/0091517 A1 | 4/2011 | Binette et al. | |
| 2011/0245929 A1 * | 10/2011 | Rakin | A61F 2/08 623/23.72 |
| 2012/0207718 A1 | 8/2012 | Stone et al. | |
| 2013/0138123 A1 | 5/2013 | Stone et al. | |
| 2013/0158601 A1 | 6/2013 | Stone et al. | |
| 2013/0338792 A1 * | 12/2013 | Schmieding | A61F 2/30756 623/23.73 |
| 2014/0017283 A1 | 1/2014 | Yoo et al. | |
| 2014/0031863 A1 | 1/2014 | Gittings et al. | |
| 2014/0142718 A1 | 5/2014 | Seyedin et al. | |
| 2014/0222162 A1 | 8/2014 | Seedhom | |
| 2015/0057750 A1 | 2/2015 | Timmerman | |
| 2015/0182233 A1 * | 7/2015 | Van Wyk | A61B 17/32002 606/80 |
| 2016/0287243 A1 | 10/2016 | Benedict et al. | |

OTHER PUBLICATIONS

Steit, Jonathan J., et al., Fresh osteochondral allograft for shoulder resurfacing relieves pain, Orthopedics Todya, Oct. 2013; six pages; https://www.healio.com/orthopedics/shoulder-elbow/news/print/orthopedics-today/%7bccb. . . .

International Preliminary Report on Patentability for International application No. PCT/US2015/059192 dated Oct. 12, 2017.

* cited by examiner

METHOD OF REPAIRING CARTILAGE DEFECTS

BACKGROUND

This disclosure relates to a surgical method for knotlessly fixating a cartilage graft to bone to repair a cartilage defect.

Repetitive trauma to a joint, such as a knee, ankle, hip or shoulder joint, may cause cartilage defects. Cartilage defects include localized areas of damaged articular cartilage and, potentially, adjacent subchondral bone. Cartilage defects typically do not heal without treatment. If not treated, the defect could further deteriorate the articulate cartilage and/or underlying bone of the joint, thereby causing relatively significant arthritic pain in some individuals.

SUMMARY

A method for repairing a cartilage defect according to an exemplary aspect of the present disclosure includes, among other things, preparing a cartilage defect for implantation of a cartilage graft and attaching the cartilage graft to bone using at least one knotless suture anchor.

In a further non-limiting embodiment of the foregoing method, the preparing step includes creating vertical margins around a periphery of the cartilage defect.

In a further non-limiting embodiment of either of the foregoing methods, the preparing step includes removing at least a portion of the cartilage defect using a curette.

In a further non-limiting embodiment of any of the foregoing methods, the preparing step includes performing bone marrow stimulation to the cartilage defect.

In a further non-limiting embodiment of any of the foregoing methods, the step of performing the bone marrow stimulation includes performing a microfracture procedure.

In a further non-limiting embodiment of any of the foregoing methods, the preparing step includes drying the cartilage defect.

In a further non-limiting embodiment of any of the foregoing methods, the attaching step includes passing a flexible strand through the cartilage graft, loading a free end of the flexible strand through a portion of the at least one knotless suture anchor, tensioning the flexible strand to approximate the cartilage graft to the bone and inserting the at least one knotless suture anchor into the bone to knotlessly fixate the cartilage graft to the bone.

In a further non-limiting embodiment of any of the foregoing methods, the inserting step includes moving an anchor body of the at least one knotless suture anchor toward the portion inside the bone to trap the flexible strand between the bone and the anchor body.

In a further non-limiting embodiment of any of the foregoing methods, the attaching step includes implanting the at least one knotless suture anchor into the bone, passing a flexible strand of the at least one knotless suture anchor through the cartilage graft and tensioning the flexible strand to approximate the cartilage graft to the bone.

In a further non-limiting embodiment of any of the foregoing methods, the tensioning step includes shuttling a free end of the flexible strand through the flexible strand to create a spliced loop around the cartilage graft.

In a further non-limiting embodiment of any of the foregoing methods, the at least one knotless suture anchor includes a first knotless suture anchor and a second knotless suture anchor. The attaching step includes implanting the first knotless suture anchor into the bone, passing a flexible strand connected to the first knotless suture anchor through the cartilage graft and tensioning the flexible strand to approximate the cartilage graft to the bone.

In a further non-limiting embodiment of any of the foregoing methods, the attaching step includes passing a second flexible strand through the cartilage graft, loading the second flexible strand through a portion of the second knotless suture anchor, tensioning the second flexible strand and inserting the second knotless suture anchor into bone.

In a further non-limiting embodiment of any of the foregoing methods, at least one of the first knotless suture anchor and the second knotless suture anchor is a soft knotless anchor assembly.

In a further non-limiting embodiment of any of the foregoing methods, at least one of the first knotless suture anchor and the second knotless suture anchor includes an eyelet.

In a further non-limiting embodiment of any of the foregoing methods, at least one of the first knotless suture anchor and the second knotless suture anchor includes a shuttle device configured to shuttle the flexible strand.

A method for repairing a cartilage defect according to another exemplary aspect of the present disclosure includes, among other things, passing a flexible strand through a cartilage graft, tensioning the flexible strand to approximate the cartilage graft relative to bone associated with the cartilage defect and inserting a knotless suture anchor into the bone to knotlessly fixate the cartilage graft to the bone.

In a further non-limiting embodiment of the foregoing method, the method includes creating a pilot hole in the bone prior to the step of inserting the knotless suture anchor.

In a further non-limiting embodiment of either of the foregoing methods, the tensioning step occurs before the inserting step.

In a further non-limiting embodiment of any of the foregoing methods, the tensioning step occurs after the inserting step.

In a further non-limiting embodiment of any of the foregoing methods, the method includes loading a free end of the flexible strand through a portion of the knotless suture anchor.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes surgical methods for repairing cartilage defects. The surgical methods include attaching a cartilage graft to bone using at least one knotless suture anchor. In some embodiments, the knotless suture anchor is implanted into bone before tensioning a flexible strand, such as a suture, to approximate the cartilage graft to the bone. In other embodiments, the knotless suture anchor is implanted into bone after tensioning the flexible strand to approximate the cartilage graft to the bone. These and other features are described in greater detail in the following paragraphs of this detailed description.

FIGS. 1-7 schematically illustrate a method of repairing a cartilage defect 10 located within a joint 12. The method is illustrated and described as an arthroscopic method; however, the method could alternatively be performed as an open procedure. The cartilage defect 10 can include osteochondral and/or chondral defects. In other words, the cartilage defect 10 may include localized areas of damaged articular cartilage and/or damaged subchondral bone of the joint 12. In one embodiment, the joint 12 is a knee joint. However, the methods of this disclosure may be used to repair cartilage defects located anywhere within the human body.

Figure 1:
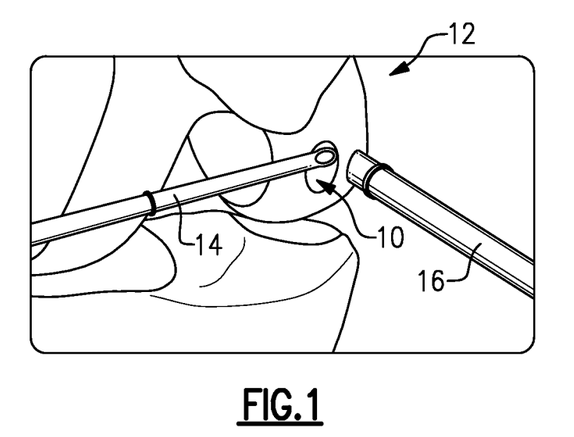
FIGS. 1 and 2 schematically illustrate preparing a cartilage defect for implantation of a cartilage graft.
Figure 3:
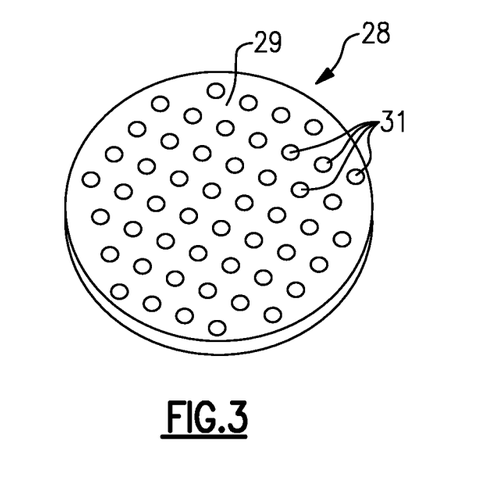
FIG. 3 illustrates an exemplary cartilage graft.

The exemplary repair method begins by prepping the cartilage defect 10 for receiving a cartilage graft 28 (shown in FIG. 3). Referring first to FIG. 1, after the surgeon has identified the cartilage defect 10 within the joint 12, the cartilage defect 10 may be debrided to a stable border having perpendicular margins. Tools, such as a curette 14 and an elevator 16, can be used to create vertical margins around a periphery of the cartilage defect 10.

Figure 2:
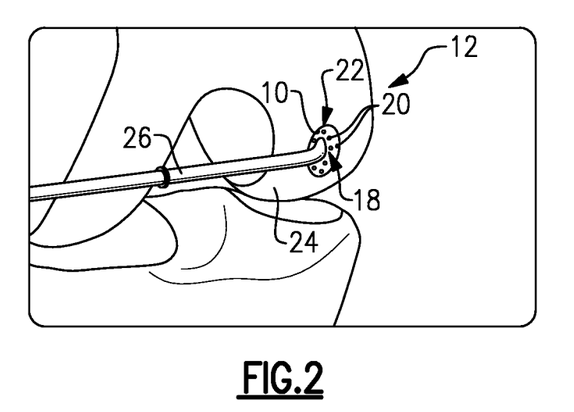

The cartilage defect 10 may be prepped with our without bone marrow stimulation. In one non-limiting embodiment, the cartilage defect 10 is further prepped by performing bone marrow stimulation. For example, as shown in FIG. 2, a microfracture procedure or some other technique may optionally be performed to obtain a bleeding bone bed 18. During the microfracture surgery, multiple perforations 20 are created in subchondral bone 22 that extends beneath the articular cartilage 24 associated with the cartilage defect 10. The bleeding bone bed 18 may be created using a tool 26, such as Arthrex's Powerpick™, to create the perforations 20. Formation of the perforations 20 creates the bleeding bone bed 18, which stimulates bone marrow seepage at the repair site. Other techniques can also be used to create the bleeding bone bed 18, including but not limited to, drilling, hammering, curetting, scraping, etc.

The cartilage defect 10 may also be dried to complete surgical preparation of the cartilage defect 10. The cartilage defect 10 is dried to remove excess moisture that could interfere with implantation of the cartilage graft 28. The cartilage defect 10 may be dried using any known technique.

The cartilage graft 28 may be knotlessly implanted after adequately prepping the cartilage defect 10. The cartilage graft 28 serves as a scaffold over the cartilage defect 10, thereby providing a tissue network that can potentially signal autologous cellular interactions. The size and shape of the cartilage graft 28 may be selected using a template that is placed over the cartilage defect 10 and marked to indicate its general size. The template may then be used to trim to cartilage graft 28 down to the desired size and shape.

One exemplary cartilage graft 28 is illustrated in FIG. 3. In one non-limiting embodiment, the cartilage graft 28 includes a cartilage disk 29 having a plurality of pores 31 formed through the cartilage disk 29. The cartilage graft 28 may be made of human tissue (e.g., allograft cartilage), synthetic materials, xeno materials, etc. In one non-limiting embodiment, the cartilage graft 28 is made of a micronized cartilage matrix. Although shown as being porous, the cartilage graft 28 is not limited to such an embodiment.

FIGS. 4A-4D illustrate a first non-limiting embodiment for knotlessly attaching the cartilage graft 28 to a bone B using a knotless suture anchor 30A. The cartilage graft 28 may be secured to subchondral bone 22 that is associated with the cartilage defect 10 and which has been previously exposed during one or more of the method steps shown in FIGS. 1 and 2.

Figure 4A:
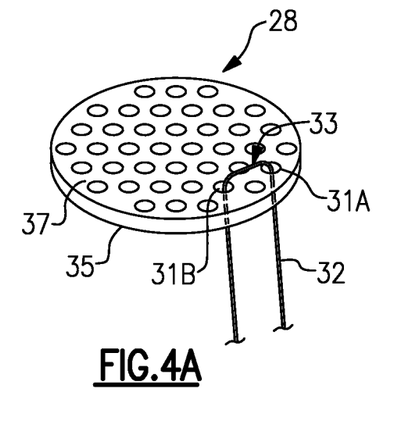
FIGS. 4A, 4B, 4C and 4D schematically illustrate knotlessly fixating a cartilage graft to bone according to a first embodiment of this disclosure.

First, as shown in FIG. 4A, a flexible strand 32, such as a suture, is passed through the cartilage graft 28. A mattress stitch 33 may be formed to connect the flexible strand 32 to the cartilage graft 28. The mattress stitch 33 is formed by inserting the flexible strand 32 through a pore 31A in a direction from the bottom 35 toward a top 37 of the disk 29 of the cartilage graft 28 and then inserting the flexible strand 32 through an adjacent pore 31B in a direction from the top 37 toward the bottom 35 of the disk 29. Other suturing techniques and configurations are also contemplated within the scope of this disclosure. For example, in situations where the cartilage graft 28 is not porous, the flexible strand 32 may be simply threaded through the cartilage graft 28.

Figure 4B:
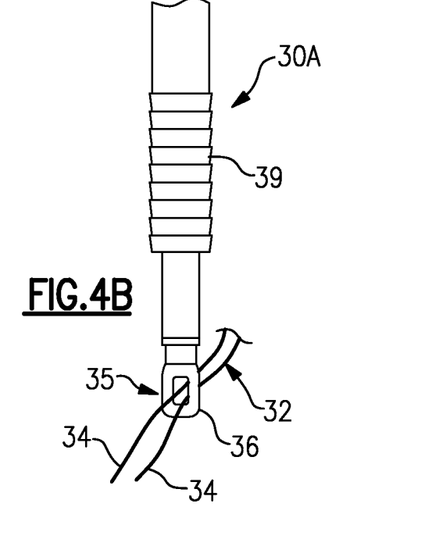
Figure 4C:
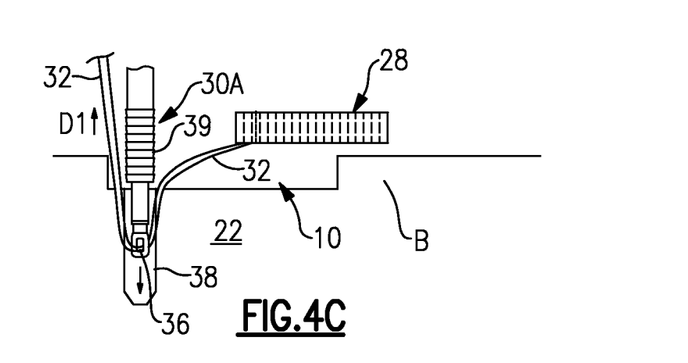

Next, as shown in FIG. 4B, one or more free ends 34 of the flexible strand 32 are loaded through a portion 35 of the knotless suture anchor 30A. In one non-limiting embodiment, the portion 35 includes an eyelet 36 of the knotless suture anchor 30A. The eyelet 36 may next be inserted into the bone B, as shown in FIG. 4C. The eyelet 36 can be inserted into a pilot hole 38 that is pre-formed in the bone B or the eyelet 36 itself can form the pilot hole 38. Once the eyelet 36 is positioned at least partially in the pilot hole 38, the flexible strand 32 may be tensioned in a direction D1 to approximate the cartilage graft 28 to the bone B. In one embodiment, tensioning the flexible strand 32 positions the cartilage graft 28 in place over the subchondral bone 22 that is associated with the cartilage defect 10.

Figure 4D:
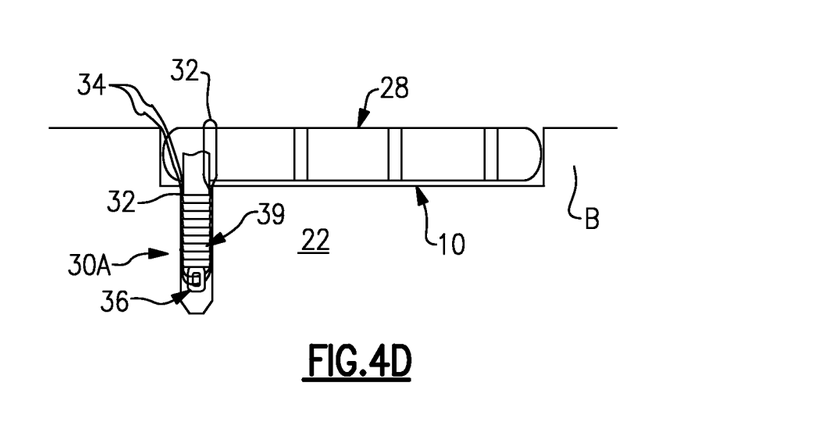

Finally, as shown in FIG. 4D, the knotless suture anchor 30A is inserted into the bone B to knotlessly fixate the cartilage graft 28 to the bone B. For example, an anchor body 39 of the knotless suture anchor 30A may be moved toward the eyelet 36 to trap the flexible strand 32 between the bone B and the anchor body 39 in order to fixate the cartilage graft 28 in place. Free ends 34 of the flexible strand 32 may be trimmed flush to the cartilage graft 28. The procedure illustrated in FIGS. 4A-4D can be repeated to implant multiple knotless suture anchors 30A to fixate the cartilage graft 28 in place.

Figure 5A:
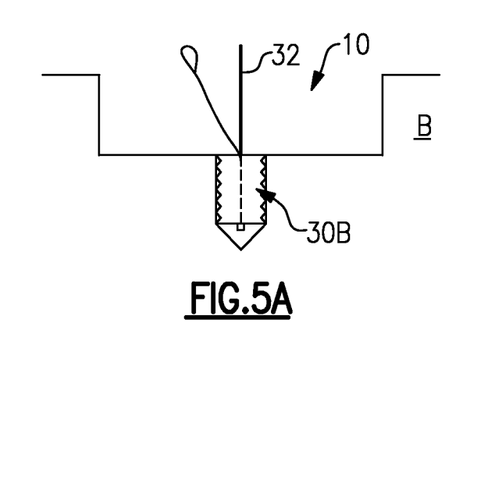
FIGS. 5A, 5B and 5C schematically illustrate knotlessly fixating a cartilage graft to bone according to a second embodiment of this disclosure.
Figure 5B:
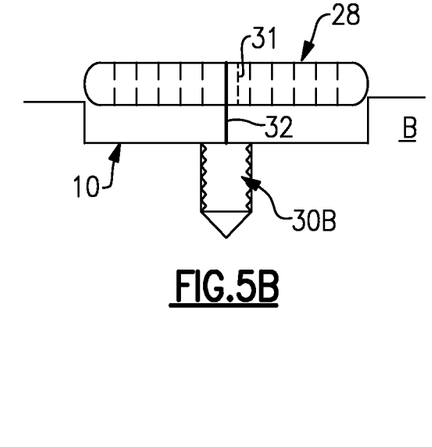
Figure 5C:
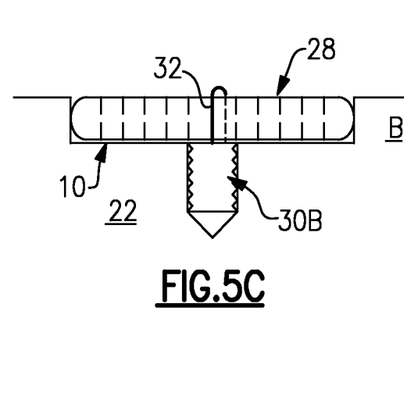
Figure 6A:
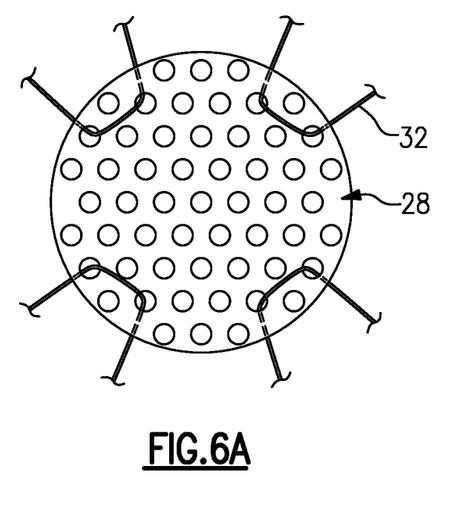
FIGS. 6A, 6B, 6C and 6D illustrate exemplary fixation patterns for fixating a cartilage graft to a bone.
Figure 6B:
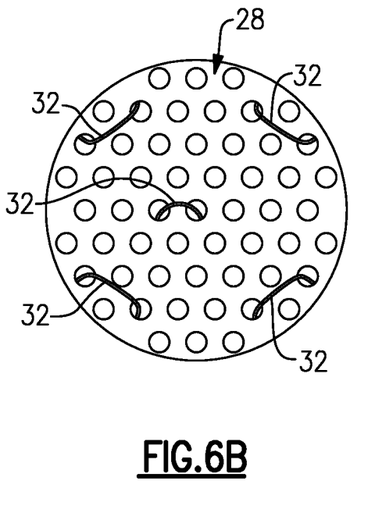
Figure 6C:
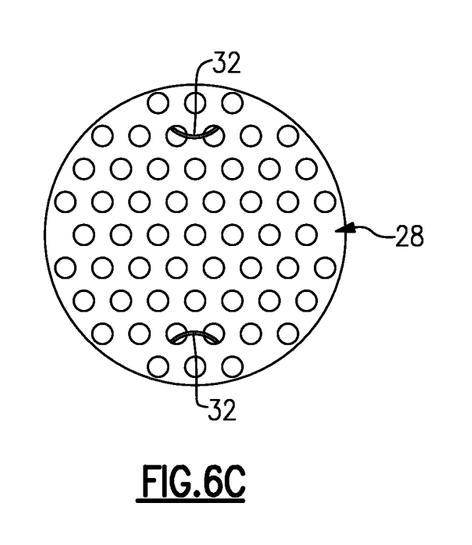
Figure 6D:
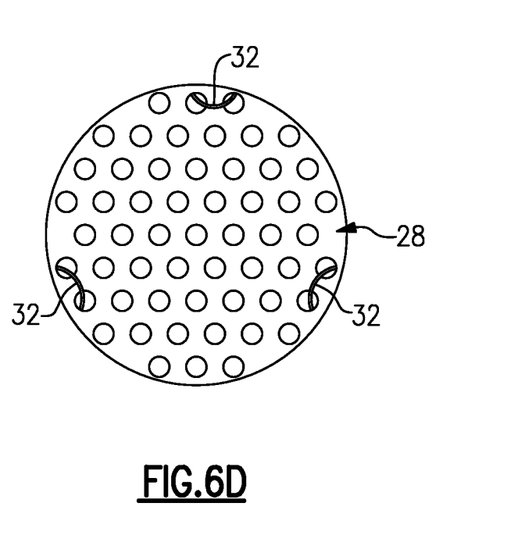

FIGS. 5A-5C illustrate another non-limiting embodiment for knotlessly fixating the cartilage graft 28 to bone B. In this embodiment, a knotless suture anchor 30B is first inserted into the bone B (see FIG. 5A). A pilot hole 38 may optionally be pre-formed into the bone B for receiving the knotless suture anchor 30B. A flexible strand 32 that is connected to the knotless suture anchor 30 may next be passed through the cartilage graft 28 (see FIG. 5B). For example, the flexible strand 32 may be looped through one or more pores 31 of the cartilage graft 28. Finally, as shown in FIG. 5C, the flexible strand 32 may be tensioned to approximate the cartilage graft 28 to the bone B. In one embodiment, tensioning the flexible strand 32 shuttles the flexible strand 32 through the knotless suture anchor 30B to tighten the cartilage graft 28 down over the subchondral bone 22 that is associated with the cartilage defect 10. The procedure illustrated in FIGS. 5A-5C can be repeated to implant multiple knotless suture anchors 30B to fixate the cartilage graft 28 in place.

The techniques shown in FIGS. 4A-4D and 5A-5C are considered "knotless" because there is no need to tie knots in the flexible strand 32 in order to secure the cartilage graft 28 to the bone B. In another non-limiting embodiment, both the technique described by FIGS. 4A-4D and the technique described by FIGS. 5A-5C may be utilized to fixate the cartilage graft 28 to the bone B. In other words, a combination of different types of knotless suture anchors may be utilized to fixate the cartilage graft 28.

Multiple different fixation patterns may be used to secure the cartilage graft 28 to the bone B. For example, the cartilage graft 28 can be fixated by positioning flexible strands 32 at each of its four quadrants (see FIG. 6A), through its center and about its periphery (see FIG. 6B), through its top and bottom halves (see FIG. 6C), or at each third of the cartilage graft 28 (see FIG. 6D). Other fixation patterns could also be used.

Figure 7:
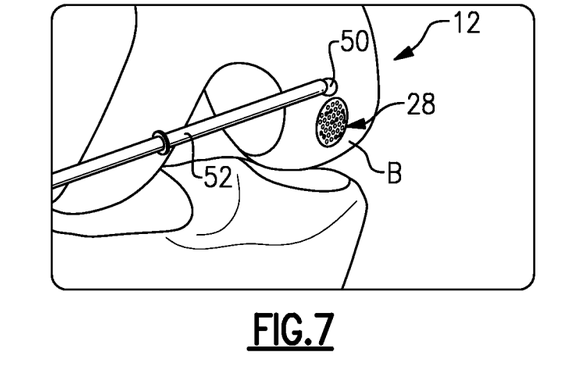
FIG. 7 illustrates applying a layer of fibrin over a repaired cartilage defect.

In another embodiment, as shown in FIG. 7, a layer of fibrin 50 may be applied over the cartilage graft 28 after it has been fixated to bone B. The fibrin 50 may be applied using an applicator 52. After the fibrin 50 and the cartilage graft 28 sit for a predefined amount of time, such as approximately five minutes, the joint 12 may be gently ranged before closure to assure adherence of the fibrin 50 and the cartilage graft 28 to the bone B.

FIGS. 8-12 illustrate exemplary knotless suture anchors that can be used in the cartilage defect repair methods described above. Knotless suture anchors similar to those shown in FIGS. 8-12 may be utilized alone or in combination with one another to fixate a cartilage graft to bone.

Figure 8:
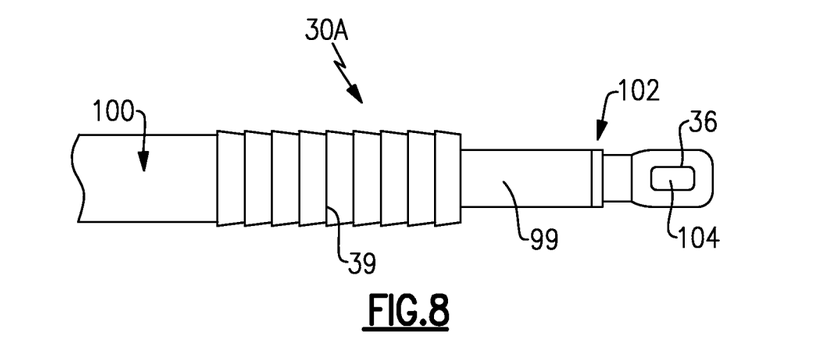
FIG. 8 illustrates a knotless suture anchor according to a first embodiment of this disclosure.

Referring first to FIG. 8, the knotless suture anchor 30A includes an anchor body 39 and an eyelet 36. The anchor body 39 is pre-loaded onto a driver 100. The anchor body 39 may be configured as a screw or an interference plug which are appropriately cannulated for receiving a shaft 99 of the driver 100. The eyelet 36 may be provided at a distal end 102 of driver 100. The eyelet 36 is releasably attached to the distal end 102 of driver 100. The eyelet 36 includes an aperture 104 for receiving one or more flexible strands (see, for example, the flexible strand 32 shown in FIG. 4B).

Figure 9:
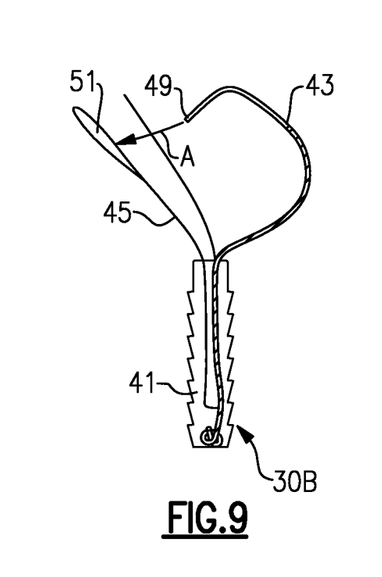
FIGS. 9 and 10 illustrate a knotless suture anchor according to a second embodiment of this disclosure.
Figure 10:
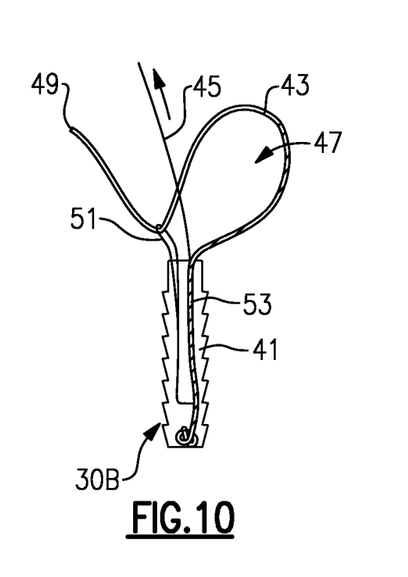

FIGS. 9-10 illustrate another knotless suture anchor 30B. In this embodiment, the knotless suture anchor 30B includes an anchor body 41 and a flexible strand 43 that extends inside of the anchor body 41. A shuttle device 45, such as a nitinol wire, is also received inside the anchor body 41. The shuttle device 45 may be pre-assembled to the flexible strand 43 as shown in FIG. 9 and will form a spliced loop 47 as shown in FIG. 10 after the flexible strand 43 is shuttled through itself. For example, a free end 49 of flexible strand 43 is passed through eyelet 51 of the shuttle device 45 (in the direction of arrow A of FIG. 9) and then the shuttle device 45 is pulled to allow flexible strand 43 to pass through itself at region 53 (see FIG. 10) and form the spliced loop 47. The perimeter of spliced loop 47 is adjustable to allow the construct to be self-cinching and to adjust the tension on the cartilage graft that is to be fixated.

Figure 11:
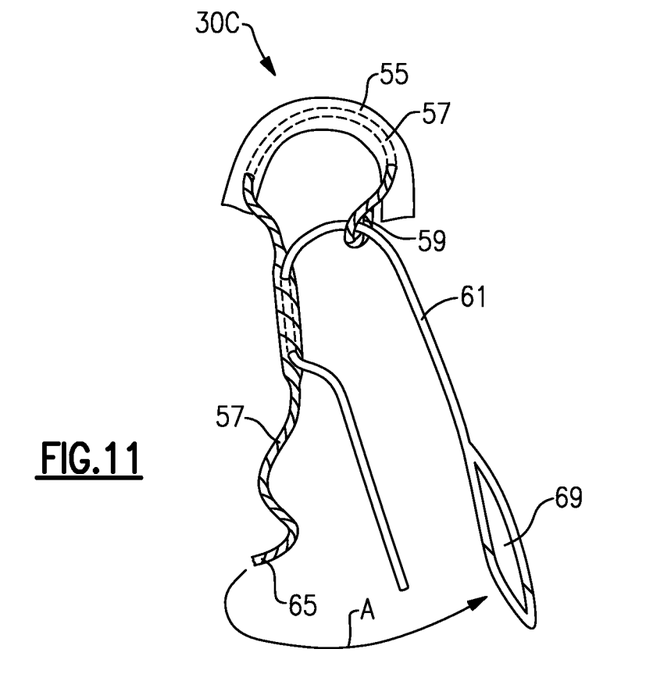
FIGS. 11 and 12 illustrate a knotless suture anchor according to yet another embodiment of this disclosure.
Figure 12:
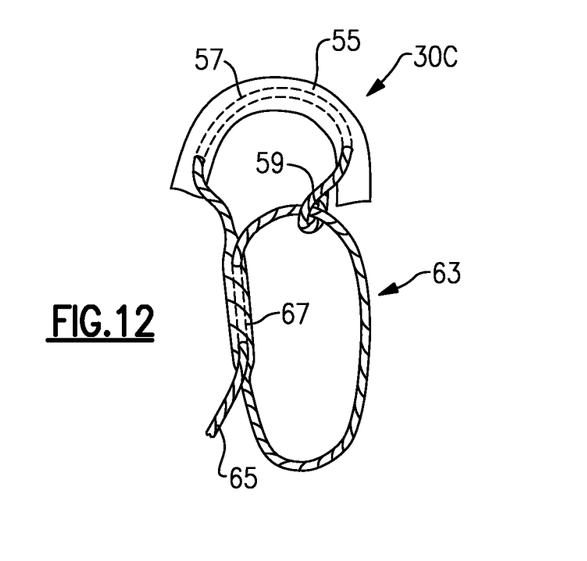

FIGS. 11-12 illustrates yet another knotless suture anchor 30C. In this embodiment, the knotless suture anchor 30C is a "soft" anchor assembly formed of soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. In one non-limiting embodiment, the knotless suture anchor 30C is made exclusively of soft, suture-based materials.

The knotless suture anchor 30C includes an anchor body 55 and a flexible strand 57 received through the anchor body 55. The flexible strand 57 includes an eyelet 59 (located at one end of the strand) that is preloaded with a shuttle device 61 attached at the portion of the flexible strand 57 that exits the anchor body 55 (for example, at a portion of the other end of the strand). In one embodiment, the shuttle device 61 is a nitinol passing wire. The shuttle device 61 may be pre-assembled to the flexible strand 57 as shown in FIG. 11 and will form a spliced loop 63 as shown in FIG. 12 after the flexible strand 57 is shuttled through itself. For example, a free end 65 of flexible strand 57 is passed through eyelet 69 of the shuttle device 61 (in the direction of arrow A of FIG. 11) and then the shuttle device 61 is pulled to allow flexible strand 57 to pass through itself at region 67 (see FIG. 12) and form the spliced loop 63. The perimeter of spliced loop 63 is adjustable to allow the construct to be self-cinching and to adjust the tension on the cartilage graft to be fixated.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method for repairing a cartilage defect, comprising:
debriding a cartilage defect to a border having vertical margins;
creating a bleeding bone bed in a subchondral bone that extends beneath an articular cartilage associated with the cartilage defect;
inserting a knotless suture anchor into the subchondral bone;
after inserting the knotless suture anchor, passing a flexible strand that is connected to the knotless suture anchor through a cartilage graft, wherein the cartilage graft includes a cartilage disk having a plurality of pores and the flexible strand is looped through at least two pores of the plurality of pores;
tensioning the flexible strand to approximate the cartilage graft to the subchondral bone;
wherein tensioning the flexible strand shuttles the flexible strand through the knotless suture anchor to tighten the cartilage graft down over the subchondral bone; and
applying a layer of fibrin over the cartilage graft.

2. The method as recited in claim 1, wherein the cartilage graft is a micronized cartilage matrix graft consisting of the cartilage disk having the plurality of pores.

* * * * *